(12) United States Patent
Wu et al.

(10) Patent No.: US 11,351,091 B2
(45) Date of Patent: *Jun. 7, 2022

(54) TRANSFER SET WITH FLOATING NEEDLE FOR DRUG RECONSTITUTION

(71) Applicant: Becton, Dickinson and Company, Franklin Lakes, NJ (US)

(72) Inventors: Haiming Wu, North Attleboro, MA (US); Richard A. Cronenberg, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 541 days.

This patent is subject to a terminal disclaimer.

(21) Appl. No.: 16/238,144

(22) Filed: Jan. 2, 2019

(65) Prior Publication Data

US 2019/0133885 A1 May 9, 2019

Related U.S. Application Data

(63) Continuation of application No. 14/377,553, filed as application No. PCT/US2013/029088 on Mar. 5, 2013, now Pat. No. 10,206,854.

(Continued)

(51) Int. Cl.
*A61J 1/20* (2006.01)
*A61J 1/14* (2006.01)
(Continued)

(52) U.S. Cl.
CPC ........... *A61J 1/2089* (2013.01); *A61J 1/1406* (2013.01); *B65B 3/003* (2013.01); *A61J 1/062* (2013.01);
(Continued)

(58) Field of Classification Search
CPC ...... A61J 1/2089; A61J 1/2013; A61J 1/2051; A61J 1/062; A61J 1/201; A61J 1/1481;
(Continued)

(56) References Cited

U.S. PATENT DOCUMENTS 3,563,373 A * 2/1971 Paulson ................ A61J 1/2093
206/229
6,209,738 B1 4/2001 Jansen et al.
(Continued)

FOREIGN PATENT DOCUMENTS

DE 1913926 9/1970
EP 1093784 A2 4/2001
(Continued)

*Primary Examiner* — Ariana Zimbouski
(74) *Attorney, Agent, or Firm* — The Webb Law Firm

(57) ABSTRACT

An adapter assembly for establishing bidirectional fluid connection between a cartridge and a vial includes a housing having an open first end adapted to engage the cartridge and a second open end adapted to engage the vial. The adapter includes a needle assembly having a first tip and a second tip, with the needle assembly disposed within the housing and at least partially supported by a needle holder. The needle assembly is movable relative to the housing from an initial position in which the first and second tip are isolated from the cartridge and vial, to an end of use position, in which first tip is engaged with the vial and the second tip is engaged with the cartridge, establishing fluid communication therebetween. The needle assembly is maintained in the initial position by a locking structure which is released by rotationally advancing the needle holder relative to the housing.

20 Claims, 19 Drawing Sheets

Related U.S. Application Data

(60) Provisional application No. 61/606,748, filed on Mar. 5, 2012.

(51) Int. Cl.
*B65B 3/00* (2006.01)
*A61J 1/06* (2006.01)
*A61M 5/315* (2006.01)

(52) U.S. Cl.
CPC .............. *A61J 1/1481* (2015.05); *A61J 1/201* (2015.05); *A61J 1/2013* (2015.05); *A61M 2005/31508* (2013.01)

(58) Field of Classification Search
CPC .................. A61J 1/1406; B65B 3/003; A61M 2005/31508
See application file for complete search history.

(56) References Cited

U.S. PATENT DOCUMENTS

| | | | |
|---|---|---|---|
| 6,319,234 B1* | 11/2001 | Restelli | A61M 5/326 604/110 |
| 10,206,854 B2* | 2/2019 | Wu | A61J 1/2089 |
| 2002/0010995 A1 | 1/2002 | Thibault et al. | |
| 2007/0088315 A1 | 4/2007 | Haindl | |
| 2008/0223484 A1 | 9/2008 | Horppu | |
| 2010/0286606 A1* | 11/2010 | Ding | A61J 1/2096 604/92 |
| 2011/0127294 A1* | 6/2011 | Pearcy | A61J 1/2089 422/501 |
| 2014/0034185 A1 | 2/2014 | Mueller et al. | |
| 2014/0311624 A1* | 10/2014 | Eilertsen | A61J 1/2089 141/18 |

FOREIGN PATENT DOCUMENTS

| | | |
|---|---|---|
| EP | 2123316 A1 | 11/2009 |
| WO | 2005074860 A1 | 8/2005 |

\* cited by examiner

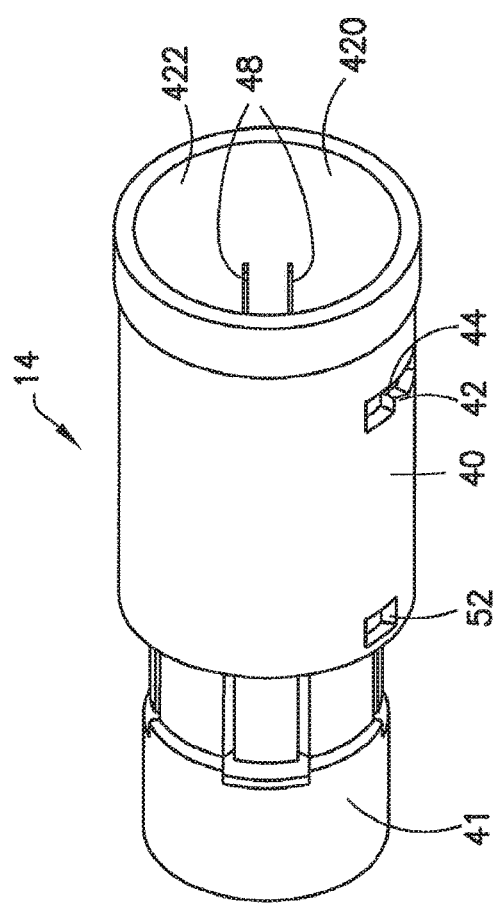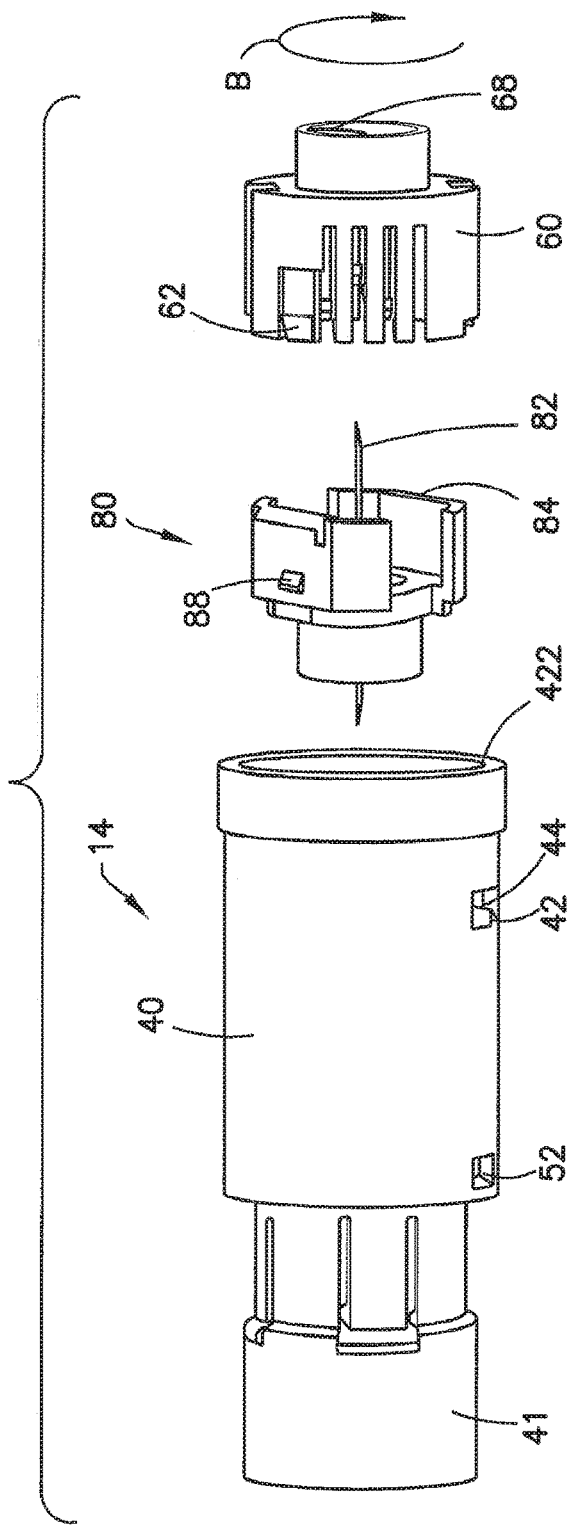

TRANSFER SET WITH FLOATING NEEDLE FOR DRUG RECONSTITUTION

CROSS-REFERENCE TO RELATED APPLICATIONS

This application is a continuation of U.S. patent application Ser. No. 14/377,553 filed Aug. 8, 2014, which is the United States national phase of International Application No. PCT/US2013/029088 filed Mar. 5, 2013, and claims priority to U.S. Provisional Application No. 61/606,748 filed Mar. 5, 2012, the disclosures of which are hereby incorporated in their entirety by reference.

BACKGROUND OF THE INVENTION

Field of the Invention

The present invention relates to drug reconstitution devices and, more particularly, to vial adapters for creating fluid communication between a cartridge and a vial to allow for reconstitution of a drug or medicament.

Description of Related Art

Certain drugs are preferably provided in powder or dry form (such as a lyophilized form), and require liquid reconstitution prior to administration to a patient. Lyophilized drugs, for example, typically are supplied in a freeze-dried form that must be mixed with a diluent to reconstitute the substance into a form that is suitable for injection.

In addition, drugs may be provided as multi-component systems which require mixing prior to administration. For example, a multi-component system may include one or more liquid (e.g., flowable) components and/or dry (e.g., powdered or granular) components which must be mixed prior to administration. Gondatopin and interferon are examples of such multi-component substances which are typically mixed just prior to being administered to a patient.

There are a number of devices and methods for drug reconstitution. The most common method is to supply a dry drug in a standard drug vial and have a medical practitioner reconstitute the drug prior to injection. The user uses a syringe to inject the diluent from one vial into a vial containing the dry drug. Next the user withdraws the reconstituted drug from the vial using a second syringe. The second syringe is used to inject the reconstituted drug into a patient. This reconstitution process is labor intensive and includes numerous opportunities for contamination of the needle and/or vial contents. Additionally, a user may accidently prick themselves or a patient with the needle while preparing the drug for reconstitution. These steps are even more intimidating for a patient attempting to self-inject a reconstituted drug for the first time.

Prior devices have also been developed that aid a user in aligning the needle of a syringe with the pierceable stopper of a vial containing the dry component of the drug. Often, the device further includes a shielding structure to prevent the user from being pierced by the needle during use.

There is a need for a reconstitution device with a safer and more accurate activation system which ensures that the needle mechanism will not be prematurely exposed or connected. Premature connection of either the drug or the diluent container to the transfer needle could lead to contamination of the drug and/or containers, or loss of drug. Unprotected exposure of the needle may also pose a safety risk.

There is also a need for a more user friendly needle advancement mechanism, which reduces the possibility of user error during the needle advancement process. It is important that the needle advancement mechanism allows for great flexibility in how and when the containers are attached to the adapter device. A further need exists for an arrangement which would allow the device to be provided: (1) as a pre-assembled kit in which the vial and cartridge come pre-attached to reduce user handling steps; (2) as a kit in which only the vial is attached; and/or (3) as a separate system in which the vial and container are attached by a user just prior to use.

SUMMARY OF THE INVENTION

Provided herein is a transfer set which receives a cartridge at one end of the cylindrical housing and a vial at the other end and allows for establishing fluid communication therebetween for mixing of the contents of each container. The device further provides a safe activation method which prevents premature release of the needle from an initial position and prevents re-exposure of the needle once reconstitution is completed. In addition, the device provides for flexibility in assembly allowing a practitioner to insert the cartridge and vial in any order and allowing for shipping of a pre-assembled product with the vial and cartridge already attached to the adapter device. A benefit of the system of the present invention is that standard pharmaceutical filing processes may be used. A further benefit of the present invention is that a user may follow standard pre-sterilization procedures with alcohol swabs prior to use.

In accordance with an embodiment of the present application, an adapter assembly for establishing bidirectional fluid connection between a cartridge and a vial includes a housing having an open first end adapted to engage the cartridge and a second open end adapted to engage the vial. The adapter also includes a needle assembly having a first tip and a second tip, with the needle assembly disposed within the housing and at least partially supported by a needle holder. The needle assembly is movable relative to the housing from an initial position in which the first tip and the second tip are isolated from both the cartridge and the vial, to an end of use position, in which the first tip is engaged with the vial and the second tip is engaged with the cartridge, thereby establishing fluid communication between the cartridge and the vial. The needle assembly is maintained in the initial position by a locking structure which is released by rotationally advancing the needle holder relative to the housing, thereby releasing the needle holder and allowing the needle holder to move axially within the housing.

In the end of use position, the first tip pierces a septum of the vial and the second tip pierces a septum of the cartridge. In certain embodiments, the locking structure includes a notch disposed within the needle holder adapted to receive a stopping rib extending from the interior wall of the housing. Rotationally advancing the needle holder aligns the stopping rib and notch to release the needle holder from the initial position allowing the needle holder to move axially within the housing. In other configurations, the locking structure includes a locking hole and riser defined within the housing and a latch tab extending from the needle holder which is engaged with the locking hole and riser when the needle holder is locked in the initial position, and which is released from the locking hole and riser when the needle holder is rotationally advanced relative to the housing.

An interior surface of the housing may include one or more longitudinal guide ribs engagable with one or more corresponding slots defined within the needle holder to support the needle holder as it moves within the housing. During transition of the needle assembly from the initial position to the end of use position, the first tip engages the vial prior to the second tip engaging the cartridge. During transition of the needle assembly from the initial position to the end of use position, the first tip may penetrate a septum of the vial prior to the second tip penetrating a septum of the cartridge. The needle holder may further include a locking tab for securing the needle holder in the end of use position.

In another embodiment of the present invention, an adapter assembly for establishing a bidirectional fluid connection between a cartridge and a vial includes a housing having an interior, an open first end adapted to engage the cartridge, and a second open end adapted to engage the vial. The adapter assembly also includes a slidable pen adapter axially movable along the interior of the housing from an initial position to an end of use position. The adapter assembly further includes a needle assembly disposed within the housing and at least partially supported by a needle holder. The needle assembly is moveable relative to the housing and capable of being advanced through the housing by the slider, wherein the slider is maintained in the initial position by a locking structure which is released by rotational advancement to allow the slider to move within the housing.

In certain configurations, the slider further includes a port adapted to receive a portion of the cartridge therein. The port may include at least one screw channel adapted to receive a corresponding screw groove defined on a portion of the cartridge. The locking structure may include a notch defined within the slider adapted to receive a stopping rib extending from the a portion of the housing, wherein rotationally advancing the slider aligns the stopping rib and notch to release the slider from the initial position allowing the slider to advance within the housing. The locking structure may include a locking hole and riser defined within the housing and a latch tab extending from the slider which is engaged with the locking hole and riser when the slider is in the initial position and which is released when the slider is rotationally advanced relative to the housing.

An interior surface of the housing may include one or more longitudinal guide ribs engagable with one or more corresponding slots defined within the needle holder to support the needle holder as it moves within the housing. The needle assembly may also include a first tip and a second tip, with the needle assembly movable relative to the housing from an initial position in which the first tip and the second tip are isolated from both the cartridge and the vial, to an end of use position, in which first tip is engaged with the vial and the second tip is engaged with the cartridge, thereby establishing fluid communication between the cartridge and the vial. The first tip may pierce a septum of the vial prior to the second tip penetrating a septum of the cartridge. The slider may also include locking tabs for connecting the slider to the needle holder in the end of use position to maintain the slider and needle holder in the end of use position once transitioned to the end of use position.

In accordance with yet another embodiment of the present invention, a transfer set for establishing a fluid connection between a vial and cartridge includes a vial having an open end, a closed bottom end, and a sidewall defining an interior, the vial having a substance disposed within the interior and a septum closing the open end. The transfer set also includes a cartridge having a cartridge port for engagement with an adapter assembly, and a plunger connected to a moveable stopper disposed within an interior of the cartridge configured to expel a liquid content from the interior of the cartridge. The transfer set also includes an adapter assembly having a housing having an open first end adapted to engage the cartridge and a second open end adapted to engage the vial. The adapter assembly includes a needle assembly having a first tip and a second tip, with the needle assembly disposed within the housing and at least partially supported by a needle holder. The needle assembly may be movable relative to the housing from an initial position in which the first tip and the second tip are isolated from both the cartridge and the vial, to an end of use position, in which first tip is engaged with the vial and the second tip is engaged with the cartridge, thereby establishing fluid communication between the cartridge and the vial. The needle assembly is maintained in the initial position by a locking structure which is released by rotationally advancing the needle holder relative to the housing, thereby releasing the needle holder and allowing the needle holder to move axially within the housing.

In certain configurations, the first tip pierces the septum of the vial prior to the second tip piercing the septum of the cartridge during transition of the needle assembly from the initial position to the end of use position.

BRIEF DESCRIPTION OF THE DRAWINGS

For the purpose of facilitating understanding of the invention, the accompanying drawings and description illustrate preferred embodiments thereof, from which the invention, various embodiments of its structures, construction and method of operation, and many advantages may be understood and appreciated.

FIG. 2 is a perspective view of the adapter assembly of FIG. 1 in accordance with an embodiment of the present invention.

FIG. 3 is an expanded perspective view of the adapter assembly of FIG. 2 in which the slider and holder are visible in accordance with an embodiment of the present invention.

DESCRIPTION OF THE PREFERRED EMBODIMENTS

Figure 1:
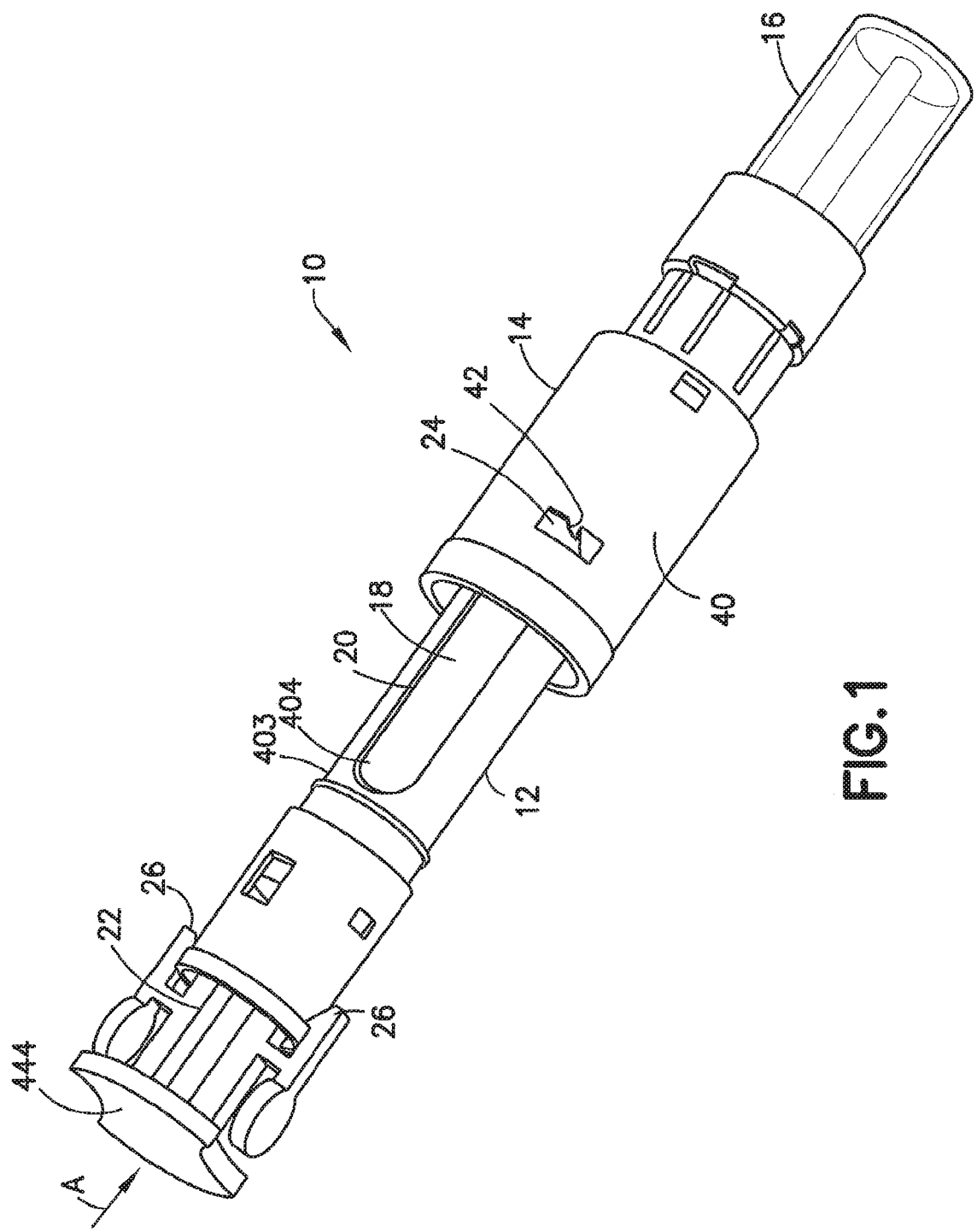
FIG. 1 is a perspective view of the transfer set of FIG. 1 with the plunger of the cartridge holder assembly in the fully compressed position in accordance with an embodiment of the present invention.

The following description is provided to enable those skilled in the art to make and use the described embodiment set forth in the best modes contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 1A:
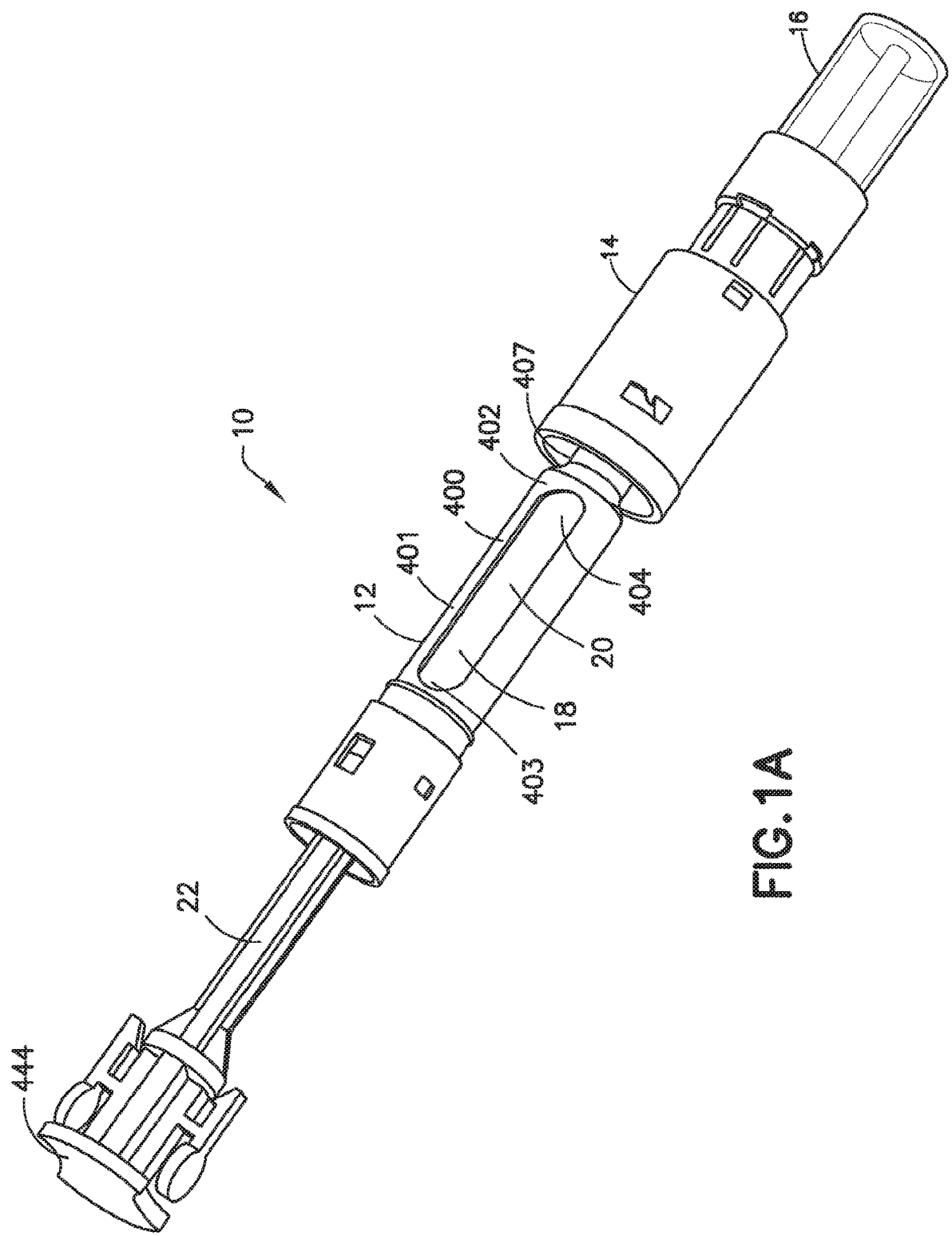
FIG. 1A is a perspective view of a transfer set including a connected vial, adapter assembly, and cartridge holder assembly in which the plunger of the cartridge holder assembly is in the initial position in accordance with an embodiment of the present invention.

With initial reference to FIGS. 1A-1, a transfer set 10 is shown which includes a cartridge holder assembly 12 and a reconstitution adapter assembly 14. Also shown are a drug vial 16 and a cartridge 18 each engaged with opposite ends of the adapter assembly 14. In one embodiment, the cartridge 18 contains a flowable substance (e.g., slurry or liquid) such as a diluent, and the vial 16 contains a dry substance intended for reconstitution (e.g., a powder or granular substance). The containers containing these substances may also be reversed. The cartridge holder assembly 12, shown in FIG. 1A in the initial position and in the compressed position in FIG. 1, as will be described herein, includes a barrel 400 of the cartridge 18 defined by a barrel wall 401 extending between a distal or forward end 402 and a proximal or rearward end 403, thereby defining an interior chamber 404 of the barrel 400 of the cartridge 18. The barrel 400 may be in the general form of an elongated cylindrical barrel as is known in the art, although other forms for containing a fluid for delivery are also contemplated by the present invention. Additionally, the barrel 400 may be formed of glass, or may be injection molded from thermoplastic material such as polypropylene and polyethylene according to techniques known to those of ordinary skill in the art, though it is to be appreciated that the barrel 400 may be made from other suitable materials and according to other applicable techniques, and may have different cross-sections (e.g. polygonal).

The barrel 400 may include markings, such as graduations on the wall 401 thereof, for providing an indication as to the level or amount of fluid contained within the barrel 400. Such markings may be provided on the external wall, the internal wall, or integrally formed or otherwise within the wall of barrel 400. Alternatively, or in addition thereto, the markings may provide a description of the contents of the syringe, or other identifying information, as may be known in the art. The cartridge holder assembly 12 may also include a viewing window 20 allowing a user to view the volume of liquid present in the interior of the cartridge 18.

The cartridge holder assembly 12 may also include a plunger 22, a portion of which is adapted to be disposed at least partially within the barrel 400 of the cartridge 18 for dispensing fluid contained within the interior of the cartridge 18. Plunger 22 provides a mechanism for extension of a 10

24 such as a plunger head which forms the base portion of the cartridge 18 for expelling fluid therefrom upon the application of a distal force to thumb press 444 located at one end of the plunger 22. All of the components of cartridge holder assembly 12 may be constructed of any known material, and are desirably constructed of medical grade polymers.

The interior of the cartridge 18 may be adapted to contain a flowable material, such as a liquid diluent or other substance intended for drug reconstitution therein. The flowable material may be a liquid or slurry component of a drug or medicament. It is further understood that the flowable material may include one or more constituent elements (e.g., two different types of drug components) containing one or more pharmacologically active agents. Alternatively, the flowable material may serve solely as a diluent for a dry drug and contain no pharmacologically active elements.

In one embodiment, the interior of the cartridge 18 may be pre-filled with the liquid diluent or other substance intended for drug reconstitution. In this manner, cartridge 18 and/or cartridge holder assembly 12 can be manufactured, pre-filled with a diluent, sterilized, and packaged in appropriate packaging for delivery, storage, and use by the end user.

Referring again to FIGS. 1A-1, the distal end 402 of the cartridge 18 terminates in a tip 407 having an outlet opening. An adapter assembly 14, as illustrated specifically in FIGS. 2-7, is provided in removable engagement with the tip 407 of the cartridge 18 and/or cartridge holder assembly 12. The adapter assembly 14 allows for the cartridge 18 and the cartridge holder assembly 12 to be coupled in fluid communication with the vial 16.

The vial 16 may be a standard drug vial of any type having an open head portion covered by a pierceable septum of an elastomeric material. The medical vial 16 contains the second component of the drug to be reconstituted. The second drug component may be provided in powdered or granular form (e.g., a lyophilized powder). Alternatively, the second component is provided in a wet form, such as a liquid or slurry, for combination with the flowable material in the cartridge 18.

The adapter assembly 14 includes a generally cylindrical body 40 defining a hollow passage 420 therethrough, and it should be noted that the body and/or passageway may have different cross-sections (e.g., polygonal). A vial receiving portion 41 adapted to engage the vial 16 is provided at a first end of the body 40 opposite a cartridge holder receiving portion 422 adapted to engage the cartridge 18. A slider 60, such as a slidable pen adapter, is adapted to slide longitudinally along a portion of the hollow passage 420 of the body 40. An engaging channel 68, such as a threaded profile, is provided on or within a top portion of the slider 60 for connecting the slider 60 to the cartridge holder assembly 12, as shown in FIGS. 1A-1, such as by corresponding threaded engagement.

Figure 4:
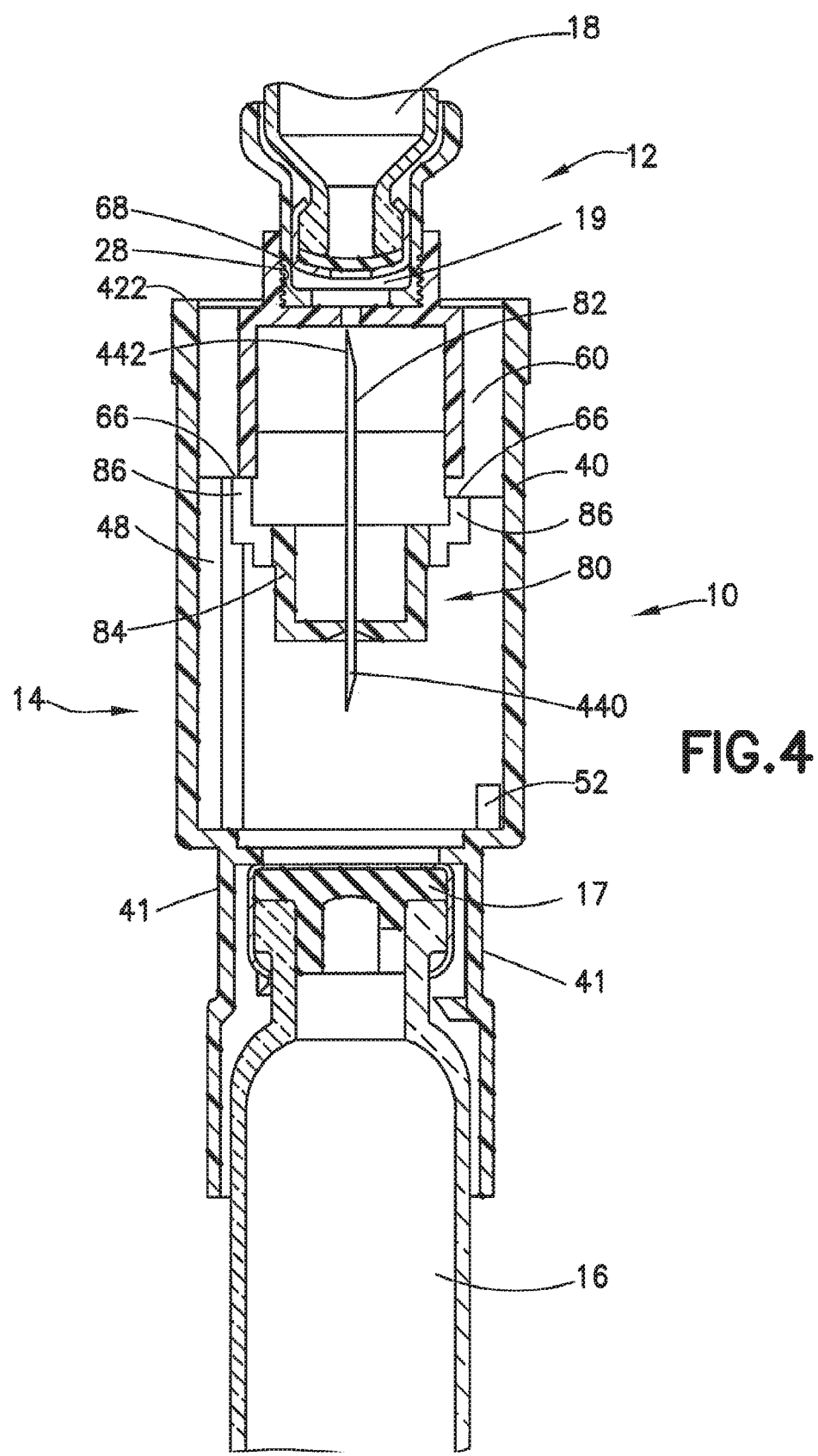
FIG. 4 is a partial cross sectional view of the transfer set of FIG. 1 with the slider and needle holder in the initial position in accordance with an embodiment of the present invention.
Figure 5:
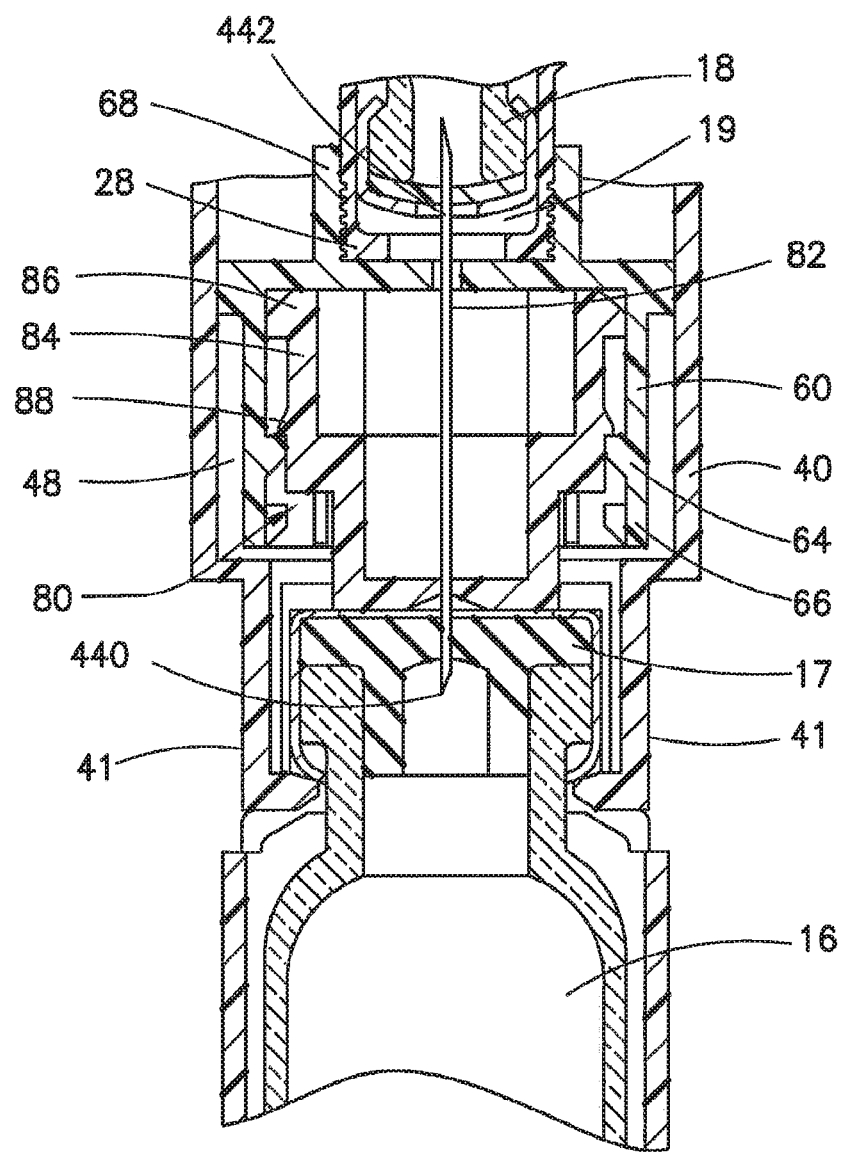
FIG. 5 is a partial cross sectional view of the transfer set of FIG. 1 in which the slider and needle holder have moved to the final end of use position and in which the needle has punctured the septum of both the cartridge and vial in accordance with an embodiment of the present invention.

As shown in FIGS. 2 and 4, guide ribs 48 are included on the interior wall of the hollow passage 420 of the body 40. The guide ribs 48 support the slider 60 which is movable from an initial position, in which the slider is disposed adjacent the cartridge holder receiving portion 422 of the body 40 as shown in FIG. 4, to a final end of use position in which the slider 60 is disposed adjacent the vial receiving portion 41 as shown in FIG. 5.

The slider 60 includes a locking tab 62, shown specifically in FIG. 3, which is engagable with a riser 42, shown in FIG. 2, defined within or connected to a portion of the body 40 and which holds the slider 60 in the initial position until the body 40 is rotationally advanced by twisting. Twisting the adapter body in the direction of arrow B, as shown in FIG. 3, forces the locking tab 62 to pass over the riser 42, thereby releasing the slider 60 and allowing the slider 60 to move longitudinally within the body 40. In effect, the riser 42 offers torque resistance requiring the user to provide sufficient rotational (e.g., twisting) force before the slider 60 is released.

Figure 6:
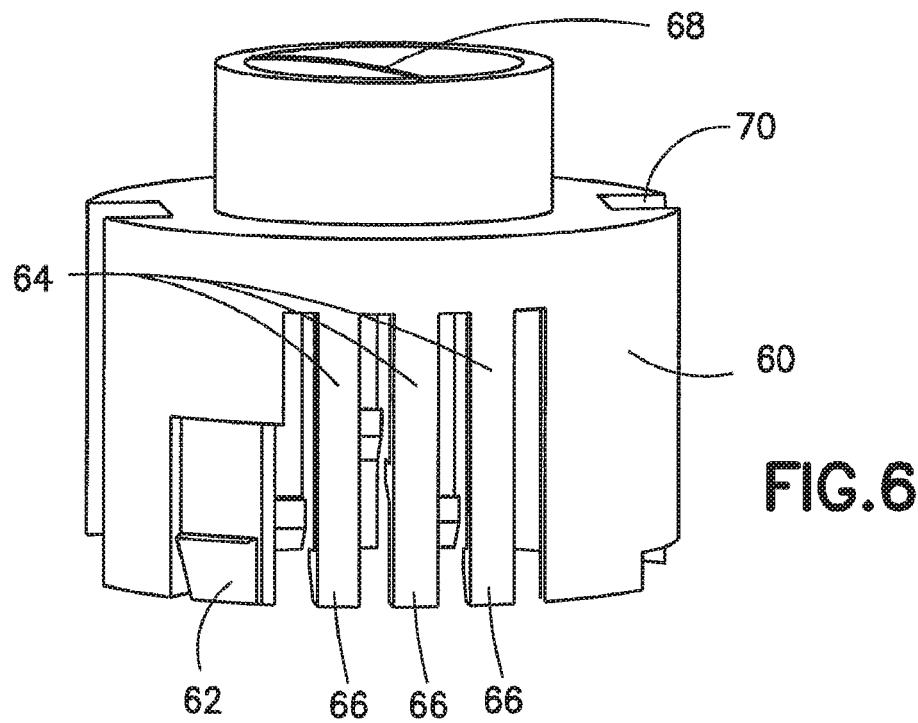
FIG. 6 is a perspective view of the slider of the adapter assembly of FIG. 2 in accordance with an embodiment of the present invention.
Figure 7:
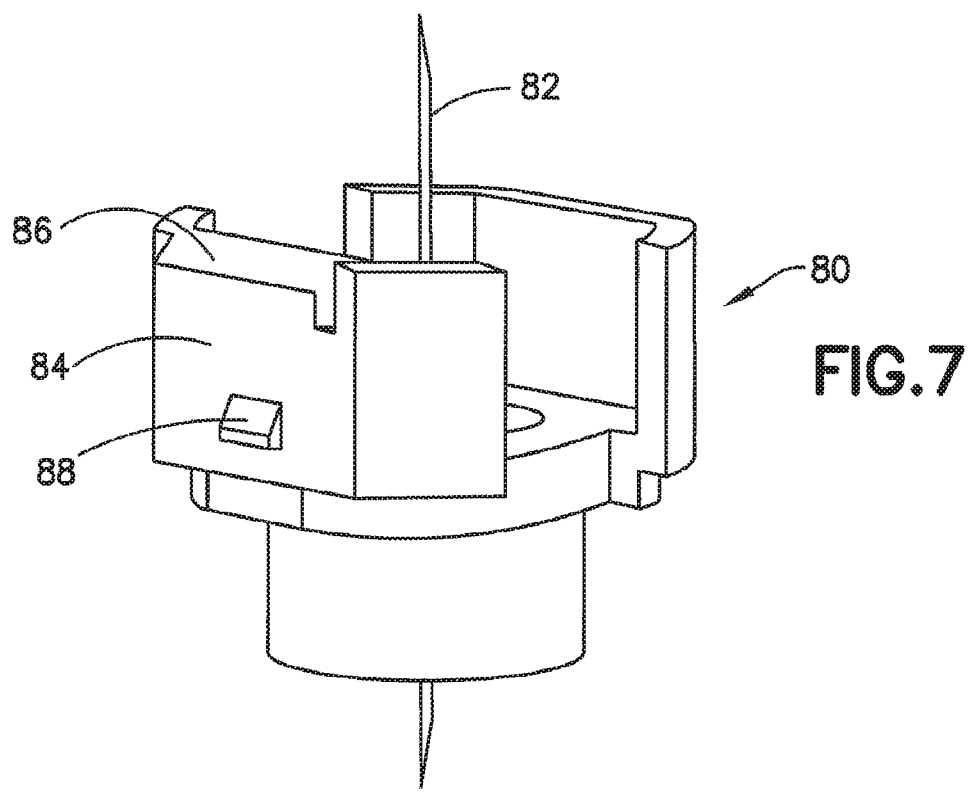
FIG. 7 is a perspective view of the needle holder of the adapter assembly of FIG. 2 in accordance with an embodiment of the present invention.

With reference now to FIG. 6, the slider 60 includes a plurality of push fingers 64 which are attached to the body of the slider 60. Assembly supports 66 are located at the free end of each of the push fingers 64. The slider 60 further includes guide channels 70 for receiving the guide ribs 48 located on the interior of the hollow passage 420 of the adapter body 40. As shown in FIGS. 4 and 5, the push fingers 64 are adapted to contact, but not substantially connect, with a needle holder 80. The needle holder 80 includes a needle assembly 82, such as a dual tipped single needle or a dual needle assembly with each needle having a single tip, and supporting structure 84. The supporting structure 84 includes a slide ledge 86. The assembly supports 66 of the slider 60 are adapted to push against the slide ledge 86 forcing the needle holder 80 to longitudinally advance distally through the hollow passage 420 of the body 40 of the adapter assembly 14. The support structure 84 also includes a needle locking tab 88 extending from the side of the needle holder 80 for securing the needle holder 80 and needle 82 to the slider 60 when the slider 60 is in the final (e.g., end of use) position. Typically, this is the most distal position of the slider 60 within the hollow passage 420. In this way, the needle holder 80 and needle 82 are prevented from being removed from the adapter assembly 14 once fluid communication is established between the cartridge 18 and vial 16, as will be discussed herein.

In use, the transfer set 10 of the present invention is assembled by attaching the vial 16 to one end of the adapter assembly 14, as shown in FIG. 1A. The cartridge holder assembly 12 is attached to the opposite end of the adapter assembly 14 by engaging an engaging portion 28, as shown in FIG. 4, such as a threaded portion of the holder assembly 12 to the corresponding engaging channel 68, or corresponding threaded portion, on the slider 60, as shown in FIG. 4. Optionally, the transfer set 10 is provided as a pre-assembled kit in which the cartridge holder assembly 12 and vial 16 are connected to the adapter assembly 14 but are not yet in fluid communication with one another through the needle 82. It is noted that the transfer set 10 of the present invention may allow for aseptic assembly of the relevant components and packaging thereof or may allow for packaging and subsequent sterilization, such as surface sterilization. Other connections of cartridge holder assembly 12 and vial 16, as well as adapter assembly 14, are possible, including snap-fit and/or bayonet-type fittings.

Once the cartridge holder assembly 12 and vial 16 are securely connected, the transfer set 10 is activated by pushing the cartridge holder assembly 12 towards the vial 16 and twisting the body 40 of the adapter assembly 14 to release the slider locking tab 62.

Following activation, the user pushes on the cartridge holder assembly 12 to advance the slider 60 through the body 40 of the adapter assembly 14. The slider 60 is supported by the guide ribs 48 which correspond to the guide channels 70 of the slider. The assembly supports 66 contact the slide ledge 86 of the needle holder 80, thereby pushing the needle holder 80 and needle 82 longitudinally along the interior wall of the body 40. Continued force on the slider 60 causes a vial end 440 of the needle 82 to contact and eventually pierce a septum 17 of the vial 16, as shown in FIG. 5. At this point, the locking tab 62 engages with an end of use lock hole 52, shown in FIGS. 2-3, located at near vial receiving portion 41 of the adapter body 40 to hold the slider 60 in this position. Similarly, the locking tabs 88 of the needle holder 80 engage with corresponding tabs on the interior of the slider 60 to secure the needle holder 80 in this position. In this way, the needle holder 80 is prevented from being removed from the adapter body 40 exposing the needle 82.

With reference again to FIG. 5, as the user continues to advance the cartridge 18 and cartridge holder assembly 12 by applying force to the slider 60, a septum 19 of the cartridge 18 is brought into contact with a cartridge end 442 of the needle 82. As pressure increases, the needle 82 pierces the septum 19 of the cartridge 18, thereby establishing fluid communication between the vial 16 and cartridge 18 through the needle 82.

At this point, the user presses down on the plunger 22 in the direction of arrow A, as shown in FIG. 1, advancing the stopper 24 within the cartridge 18. The stopper 24 expels the contents of the cartridge 18, typically a liquid, into the vial 16. Once the liquid is entirely injected into the vial, the user may shake the transfer set 10 to mix the dry and liquid components of the drug. In some embodiments, mixing may be accomplished in a matter of seconds whereas in other embodiments mixing can take as long as 20 minutes. The user can determine how much fluid has been expelled from the cartridge 18 by observing the fluid level through the viewing window 20 of the cartridge 18. The user also can tell that all fluid has been expelled from the cartridge 18 when the stopper 24 is at the base of the cartridge 18 and the plunger cannot be further advanced. The amount of mixing required is based on the composition, solubility, and viscosity of the dry and liquid components initially present in the vial 16 and cartridge 18 to be reconstituted.

Latch tabs 26, as shown specifically in FIG. 1, restrain the plunger 22 in the compressed position once the liquid has been expelled from the cartridge 18. The latch tabs 26 may also be configured to release the plunger 22 so that the drug can be drawn back into the cartridge 18 once mixing is completed. After mixing, the user inverts the device and pulls the plunger 22 in the opposite direction (opposite the direction of arrow A as shown in FIG. 1 and away from the vial and adapter assembly) to draw the mixed drug back into the cartridge 18 via suction. At this point, the user may disengage the plunger 22 from the stopper 24, such as by disengaging the threaded engagement therebetween, and removes the cartridge 18 from the cartridge holder assembly 12.

The cartridge 18 containing the reconstituted drug can then be loaded into an injection apparatus, such as a pen injector or autoinjector for injection into a patient. The drug vial 16 and adapter assembly 14, which are still connected together, can then be discarded. Advantageously, since one end of the needle 82 is still inserted into the vial 16 and the other end is enclosed within the adapter assembly 14, the device can be disposed of without exposing the needle. Therefore, there is no danger that the user will be pierced by the needle 82 while removing the cartridge 18 or otherwise handling the device.

Figure 8:
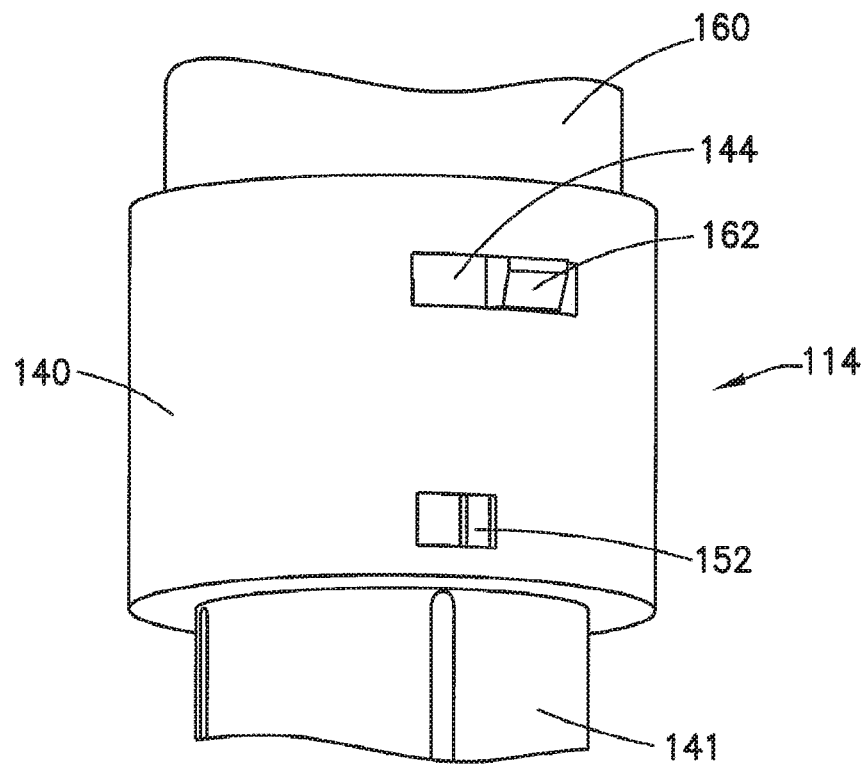
FIG. 8 is a partial perspective view of an adapter assembly having a twist lock mechanism in accordance with an embodiment of the present invention.
Figure 9:
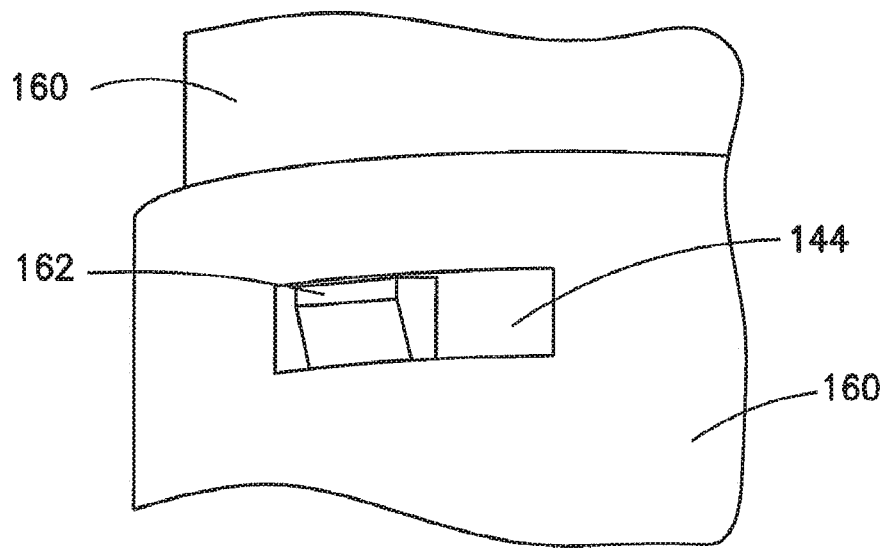
FIG. 9 is a partial perspective view of the adapter assembly of FIG. 8 having a twist lock mechanism in accordance with an embodiment of the present invention.
Figure 10:
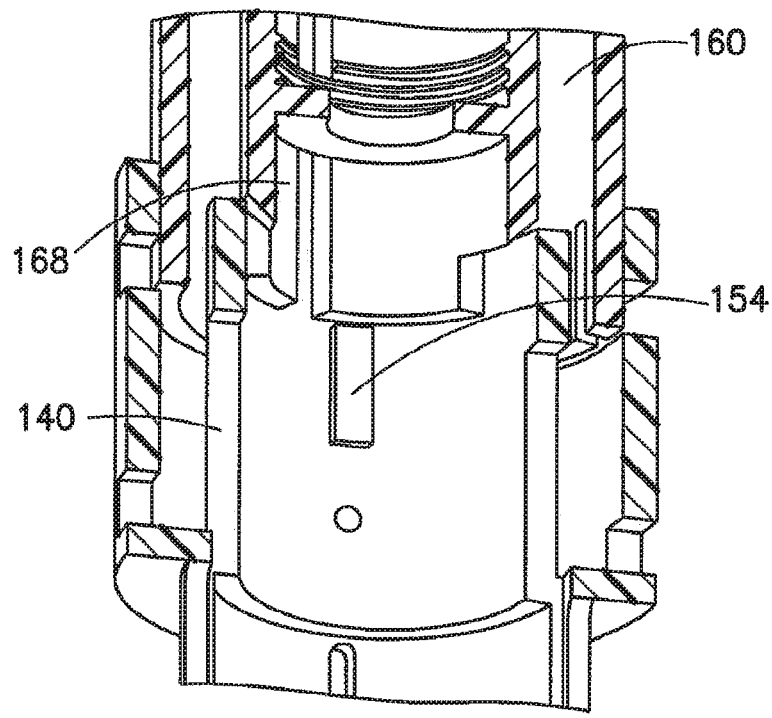
FIG. 10 is a partial cross-sectional perspective view of the interior portion of the adapter assembly of FIG. 8 with the needle holder removed so that the stop rib and place of connection between the cartridge holder and vial adapter is visible in accordance with an embodiment of the present invention.

With reference to FIGS. 8-11, another embodiment of an adapter assembly 114 is shown including a slider 160 and a cylindrical body 140 defining a hollow passage therethrough. The body 140 includes a vial receiving portion 141 located at one end of the body 140. A stop rib 154 extends from the inner wall of the body 140. The stop rib 154 replaces the riser 42 of the embodiment described above and depicted in FIGS. 1A-7. Instead, as shown in FIGS. 8 and 9, a locking tab 162 extends from the side of the slider 160 and sits in a side assembly lock hole 144 cut from the body 140. In use, the slider 160 is prevented from moving along the length of the body 140 until a cartridge holder assembly 112 is rotated. Rotation aligns the stop rib 154 of the body 140 with a notch 168 cut into the slider 160. Once the stop rib 154 and notch 168 are aligned, the slider 160 can be moved through the body 140. As similarly described in the embodiment of FIGS. 1A-7, the locking tab 162 slides into an end of use lock hole 152 at the vial end of the body 140 to prevent the user from removing the slider 160 and a needle holder 180 from the adapter assembly 114 after reconstitution has been completed.

Figure 11:
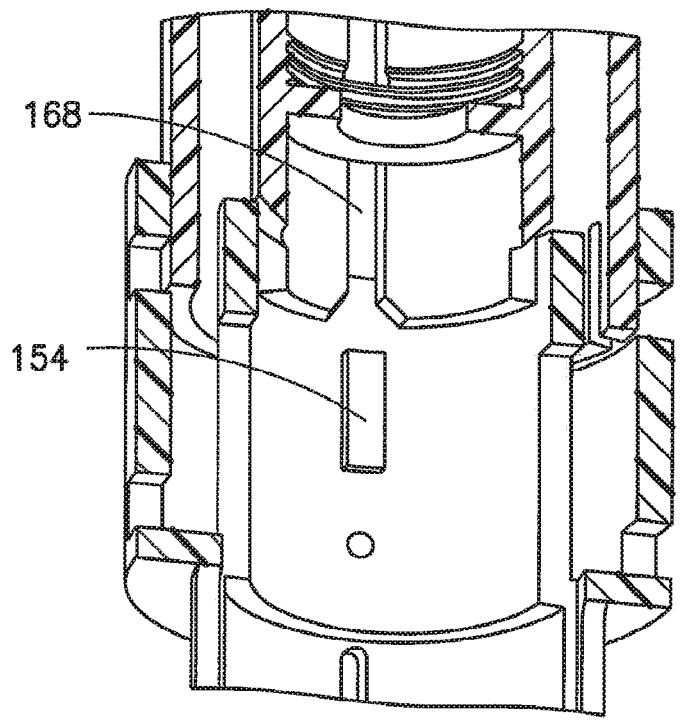
FIG. 11 is a partial cross-sectional perspective view of the interior portion of the adapter assembly of FIG. 8 with the needle holder removed so that the stop rib and place of connection between the cartridge holder and vial adapter is visible in accordance with an embodiment of the present invention.
Figure 11A:
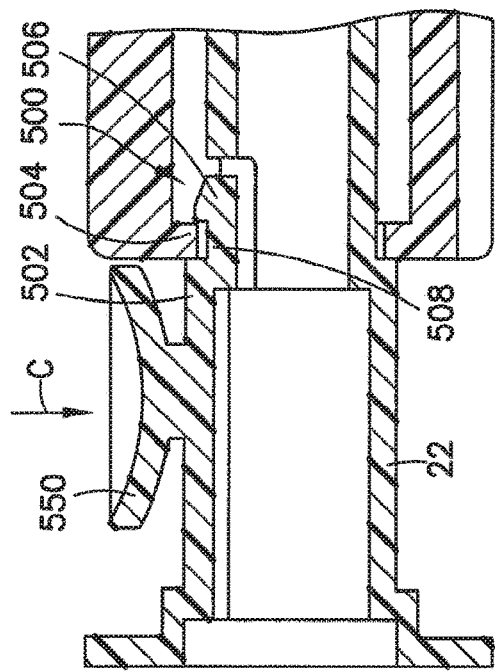
FIG. 11A is a partial cross-sectional side view of the plunger of FIG. 1 in a locked position in accordance with an embodiment of the present invention.
Figure 11B:
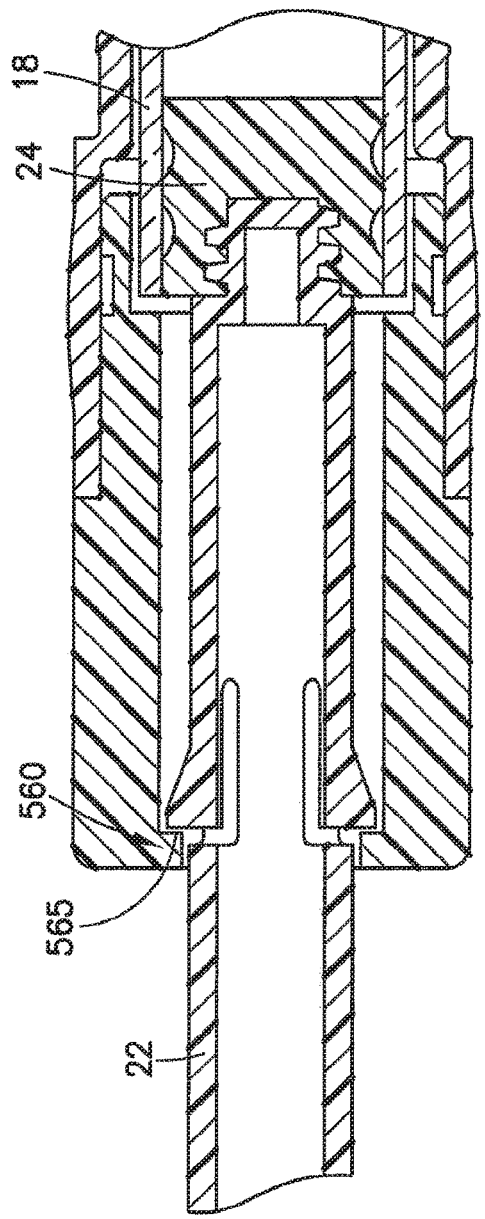
FIG. 11B is a partial cross-sectional side view of the plunger of FIG. 1 engaged to prevent inadvertent withdrawal in accordance with an embodiment of the present invention.
Figure 12:
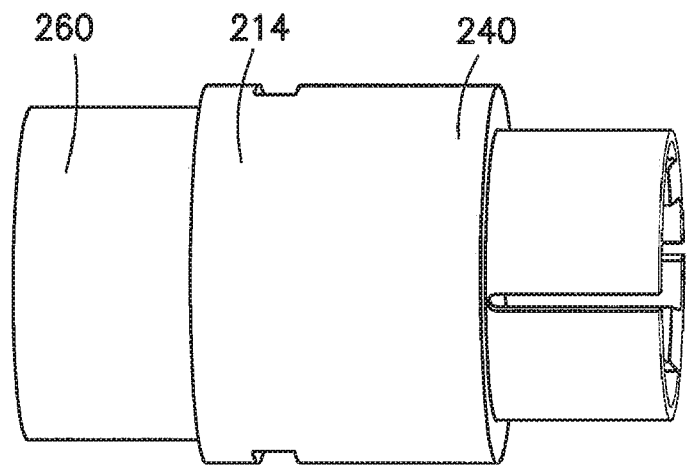
FIG. 12 is a perspective side view of an adapter assembly in accordance with an embodiment of the present invention.

With reference to FIGS. 11A-11B, when the user pushes the plunger 22 to transfer the diluent from the cartridge 18 to the vial 16, as shown in FIGS. 1A-1, there will be a back pressure on the plunger 22. To maintain the plunger 22 in the compressed position, a latch 500 may be provided between a proximal end 502 of the plunger 22 and a plunger back stop 504 of the cartridge holder assembly 12. In this configuration, the latch 500 may include a ramped portion 506 of the proximal end 502 of the plunger 22 adjacent a recess 508 adapted to receive and restrain the plunger back stop 504 thereagainst. Once the drug has been fully mixed, the latch 500 may be released by deploying the button 550 in the direction of arrow C, as shown in FIG. 11A, and the plunger 22 may be pulled from within the cartridge 18 to the initial position. As shown in FIG. 11B, the plunger 22 may also include a stop 560 capable of engaging a plunger back stop 504 to prevent the user from inadvertently pulling too far and removing the stopper 24 from the cartridge 18.

Figure 13:
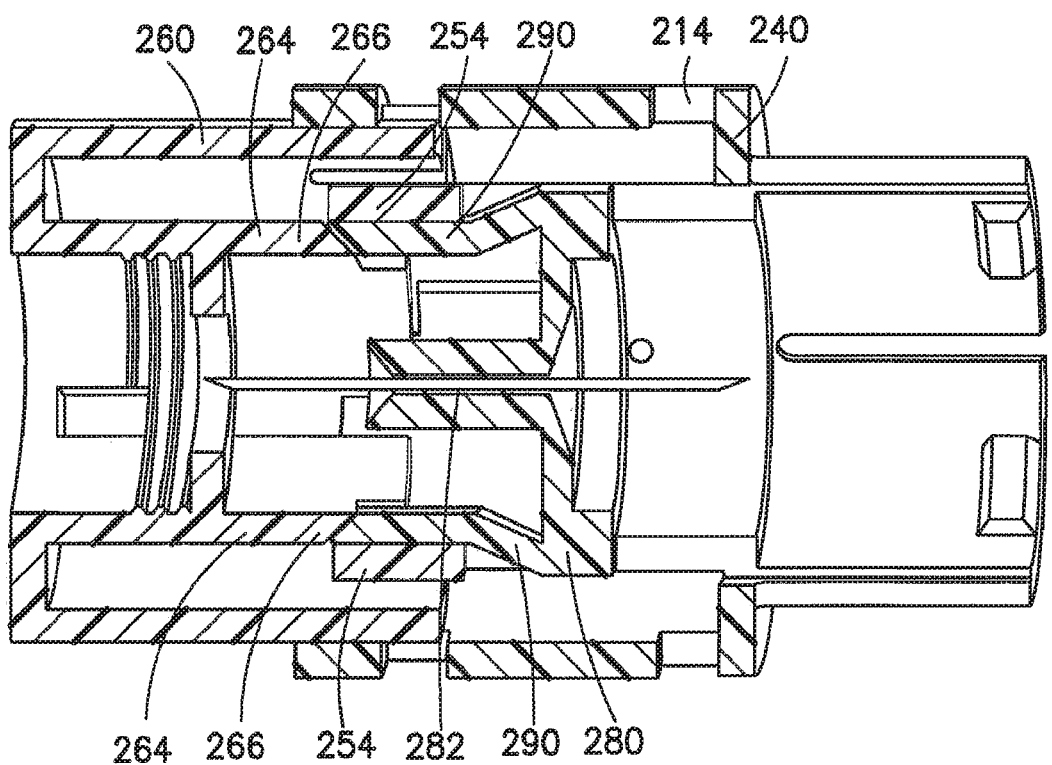
FIG. 13 is a cross-sectional perspective side view of the adapter assembly of FIG. 12 in accordance with an embodiment of the present invention.
Figure 14:
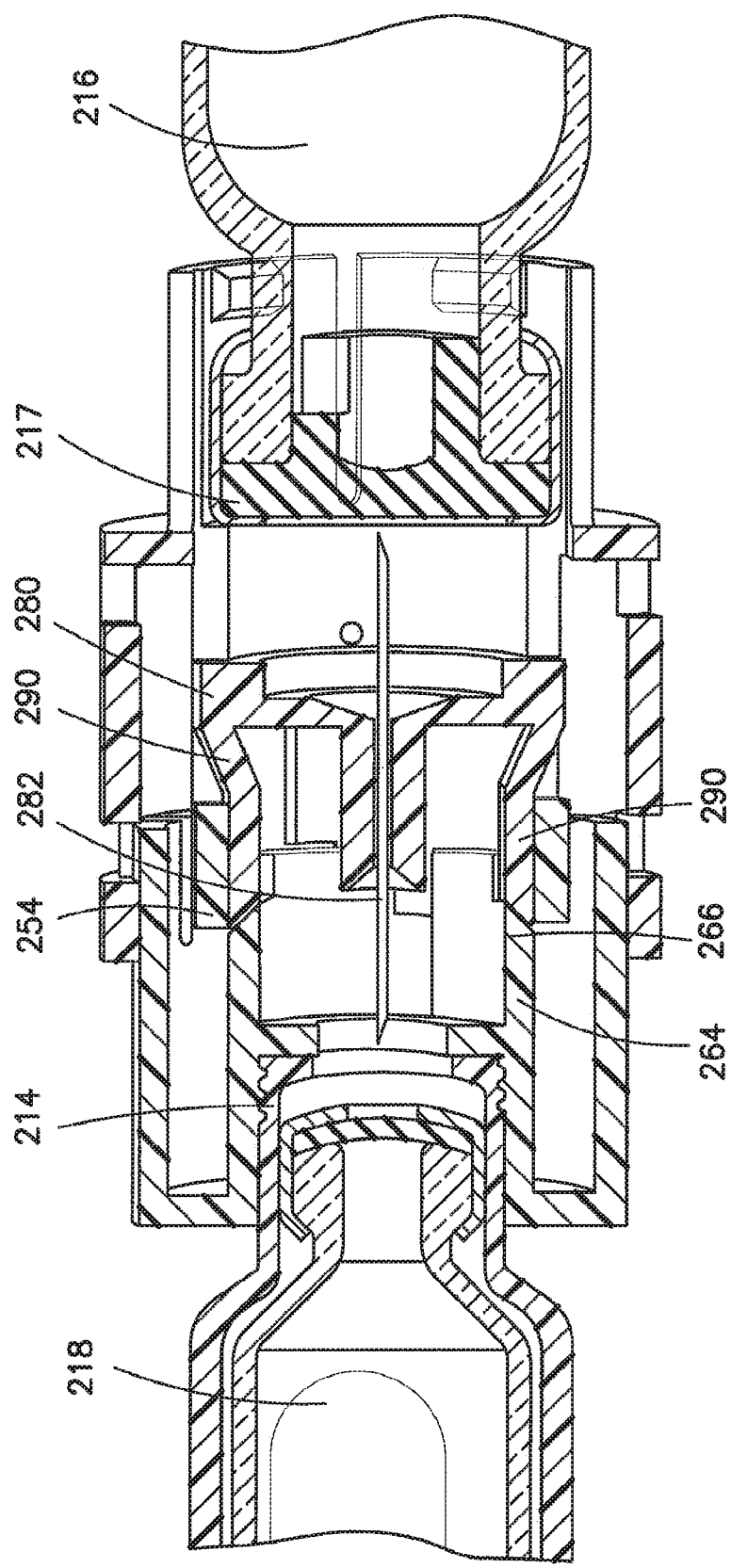
FIG. 14 is a partial cross-sectional perspective view of the adapter assembly of FIG. 12 engaged with a cartridge and a vial with the needle isolated from both the vial and the cartridge in accordance with an embodiment of the present invention.
Figure 15:
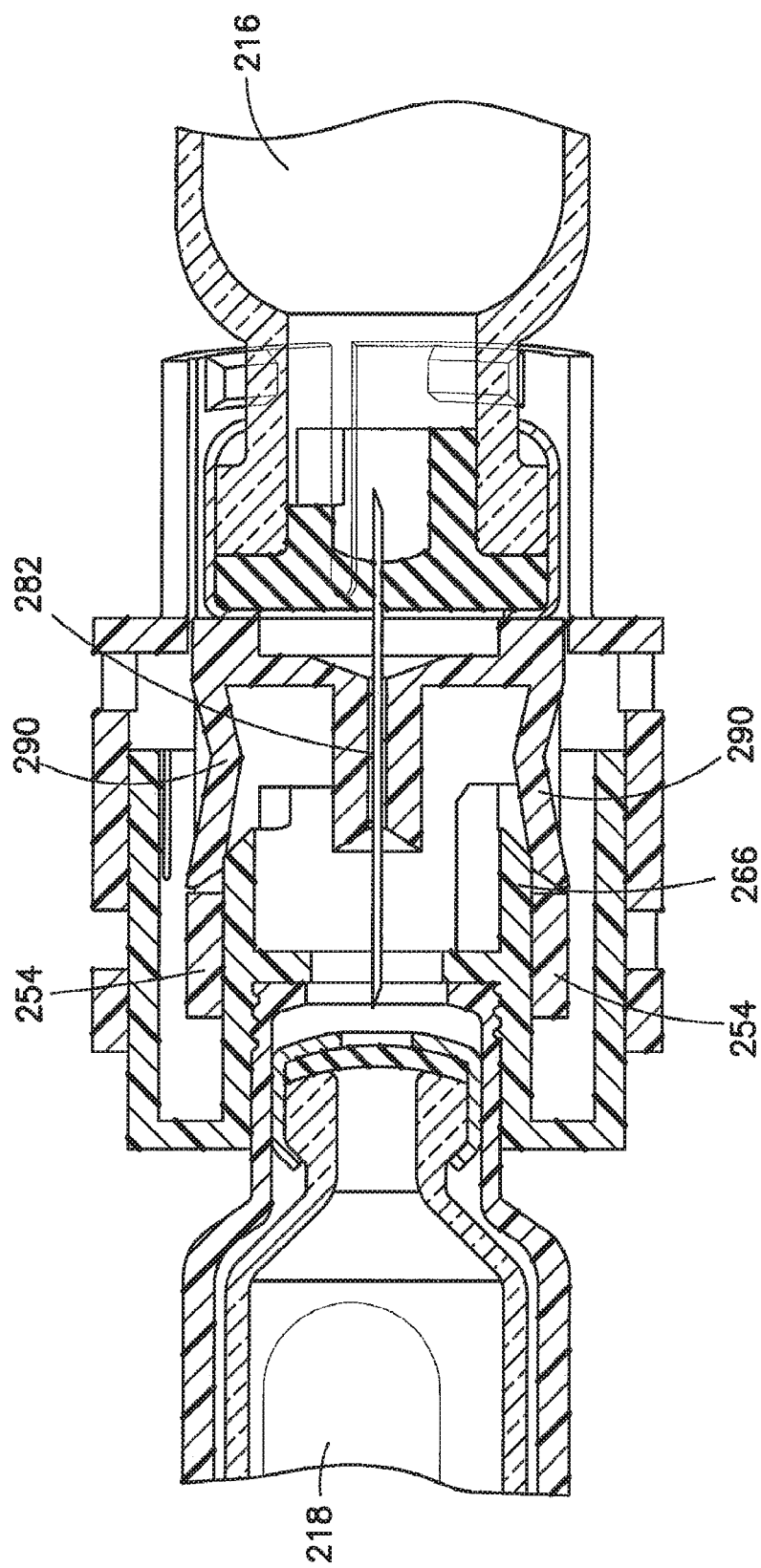
FIG. 15 is a partial cross-sectional perspective view of the adapter assembly of FIG. 12 engaged with a cartridge and a vial with the needle isolated from the cartridge and piercing the vial in accordance with an embodiment of the present invention.
Figure 16:
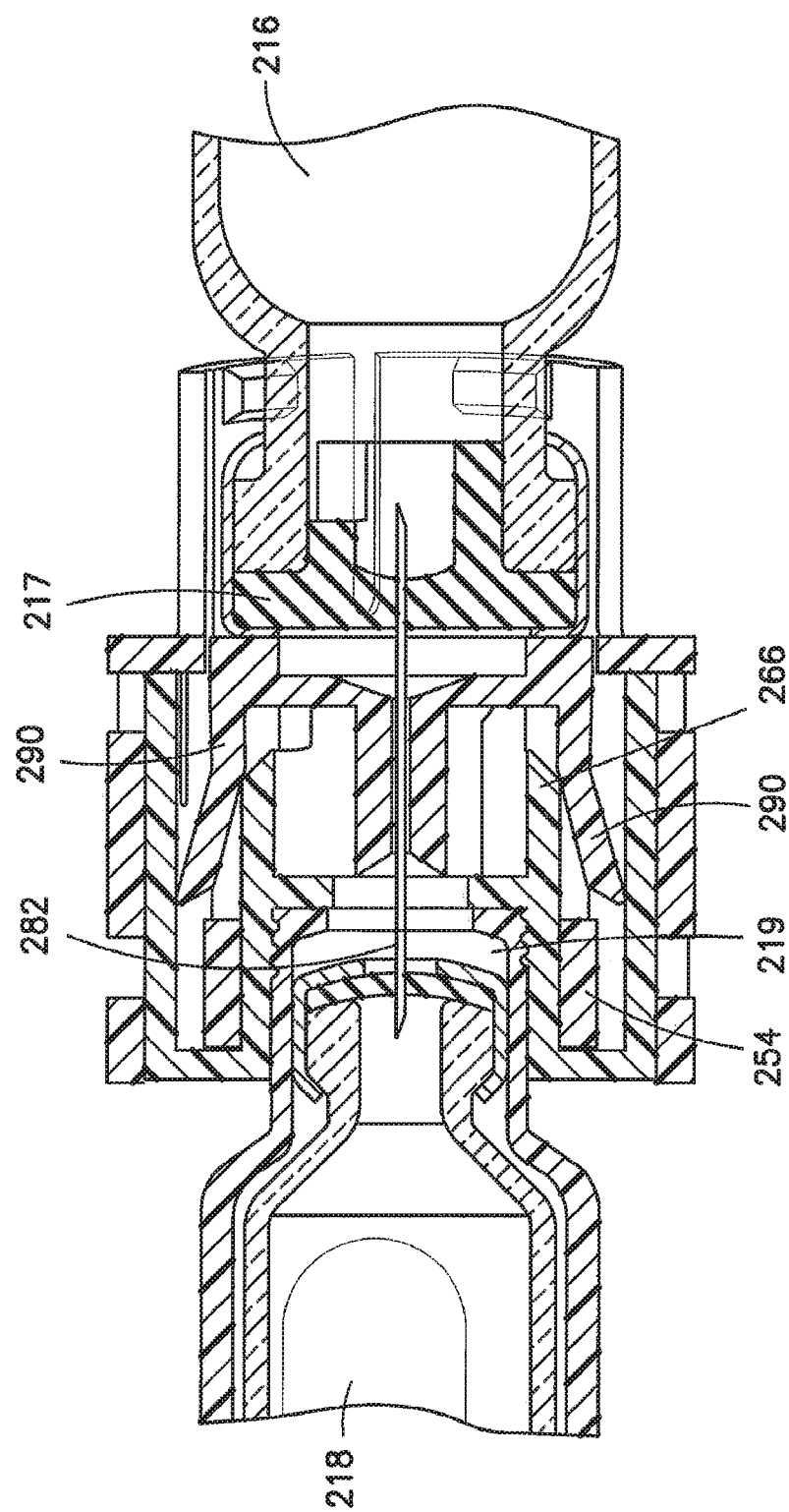
FIG. 16 is a partial cross-sectional perspective view of the adapter assembly of FIG. 12 engaged with a cartridge and a vial with the needle piercing both the vial and the cartridge to establish fluid communication therebetween in accordance with an embodiment of the present invention.
Figure 17:
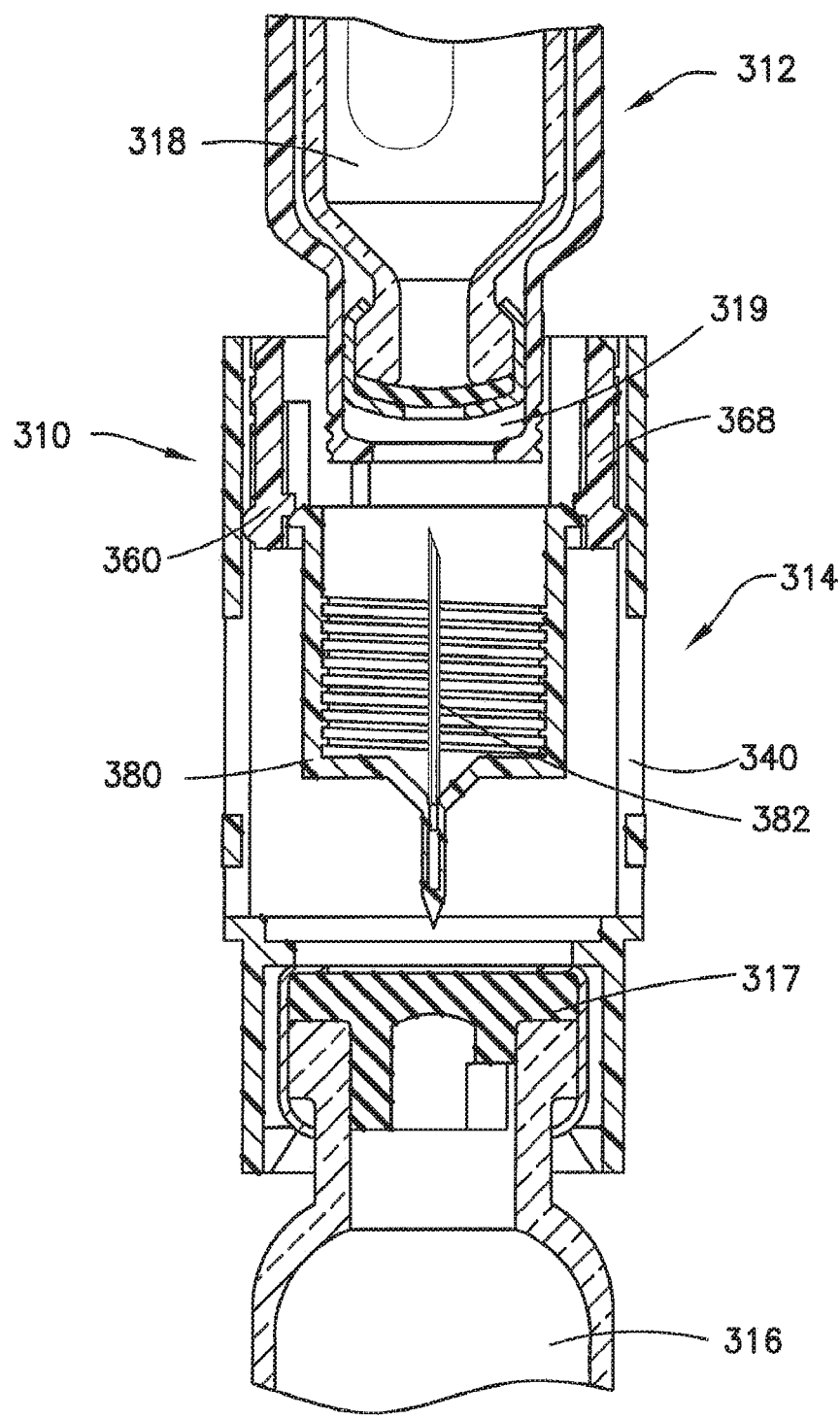
FIG. 17 is a partial cross-sectional front view of a transfer set having primary and secondary expansion windows in accordance with another embodiment of the present invention.
Figure 18:
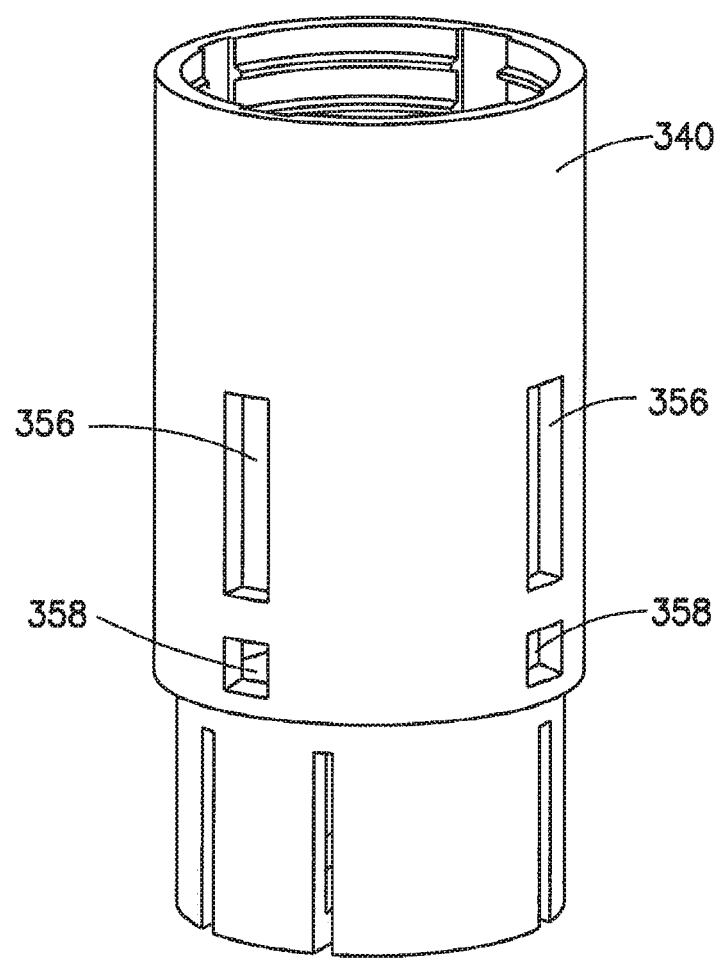
FIG. 18 is a perspective view of the adapter assembly of the transfer set of FIG. 17 in accordance with an embodiment of the present invention.

With reference to FIGS. 12-16, another embodiment of an adapter assembly 214 is illustrated including a cartridge adapter 260, a vial adapter 240, and a needle holder 280. In this embodiment, the needle holder 280 includes flexible arms 290, rather than a slide ledge. As shown in FIG. 13, in the initial (e.g., ready to use) position, the flexible arms 290 of the needle holder 280 rest against assembly supports 266. The assembly supports 266 are connected to the cartridge adapter 260 by push fingers 264. As shown in FIG. 14, as the cartridge adapter 260 and vial adapter 240 are compressed together, a needle 282 is moved towards a vial 216. The flexible arms 290 are constrained by holding ribs 254 included on the vial adapter 240. As additional pressure is applied to the cartridge adapter 260 and vial adapter 240, the needle first punctures a septum 217 of the vial 216, as shown in FIG. 14. As shown in FIG. 14, the flexible arms 290 on the needle holder are still being constrained by the holding ribs 254. As shown in FIGS. 15 and 16, once the needle holder 280 is fully bottomed against the drug vial 216, the flexible arms 290 are no longer constrained by the holding ribs 254. The flexible arms 290 begin to spread allowing the cartridge adapter 260 to bypass the arms 290 and to puncture a septum 219 of a cartridge 218.

With reference to FIGS. 17-23, a further embodiment of a transfer set 310 is illustrated including a cartridge holder assembly 312 and a reconstitution adapter assembly 314. The cartridge holder assembly 312 is similar to the holder assembly 12 described according to FIGS. 1A-7. The adapter assembly 314 includes a cylindrical body 340 defining a hollow passage, a ring slider 360, and a float hub 380 with a transfer needle 382. The body 340 has both a primary expansion window 356 and a secondary expansion window 358. The ring slider 360 includes push fingers 364 and holding fingers 368 extending from the ring portion of the ring slider 360. The push fingers 364 advance the float hub 380 through the body 340 towards a vial 316. The holding fingers 368 attach the ring slider 360 to the float hub 380 to prevent re-exposure of the needle 382 after reconstitution is complete. The sliding ring 360 further includes locking tabs 362 which engage with the expansion windows (356, 358) of the body 340 to guide the sliding ring 360 through the body 340 and to lock the sliding ring 360 in an end of use position.

Figure 19:
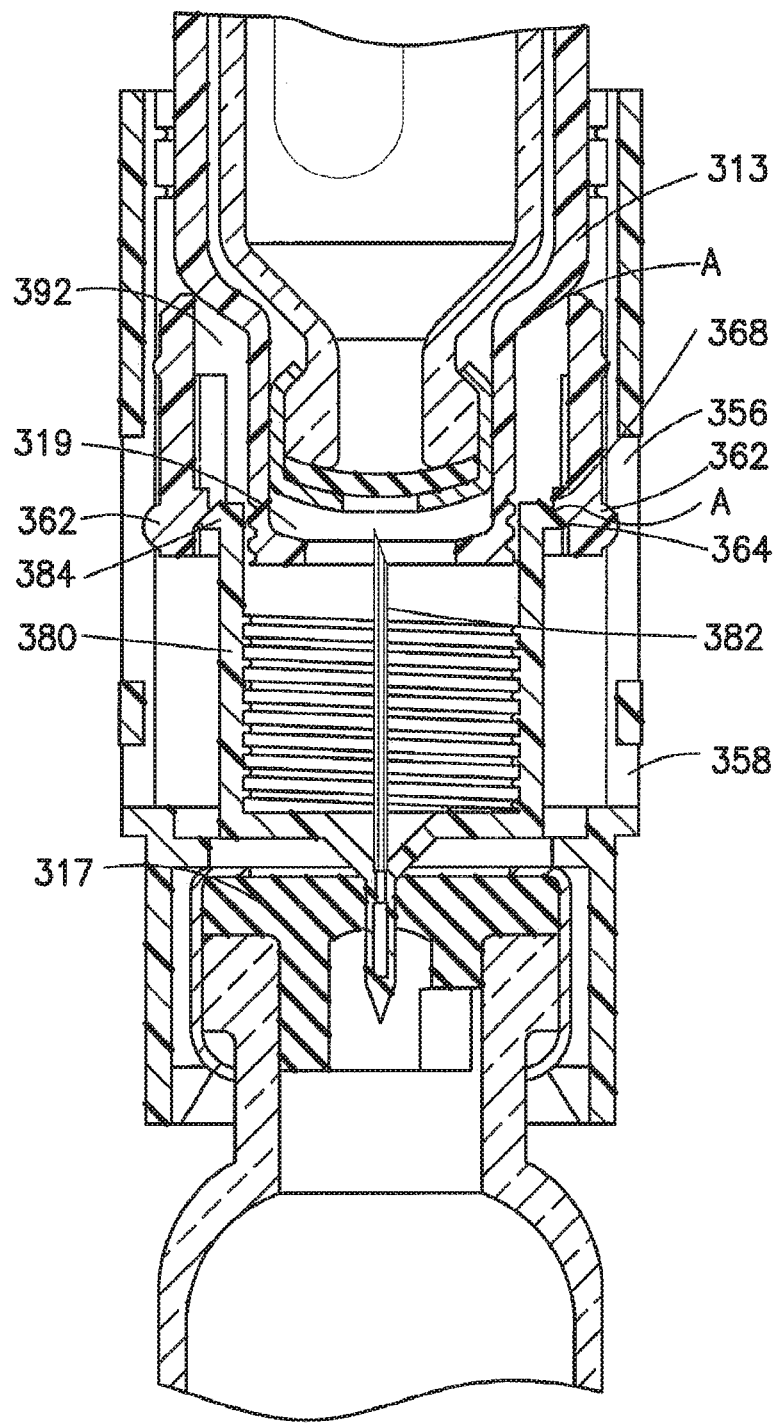
FIG. 19 is a partial cross-sectional front view of the transfer set of FIG. 17 in which the ring slide and cartridge have been advanced towards the vial in accordance with an embodiment of the present invention.

In use, the cartridge holder assembly 312 is pushed through the adapter body 340. The holder assembly 312 contacts the sliding ring 360 at load transmitting points A, as shown in FIG. 19, near shoulders 313 of the holder assembly 312 for pushing the sliding ring 360 through the assembly body 340. Advancing the sliding ring 360 brings the push fingers 364 into contact with needle holder tabs 384, thereby advancing the float hub 380 through the body 340 as well. A cartridge 318 can be brought into contact with the needle 382 by continuing to longitudinally advance the cartridge holder assembly 312 towards the vial 316. At this point, the needle 382 pierces a septum 317 of the vial 316. Continuing to rotate the cartridge 318 brings the needle holder to a final position in which the needle 382 pierces a septum 319 of the cartridge 318 to establish fluid communication between the vial 316 and cartridge 318.

Figure 20:
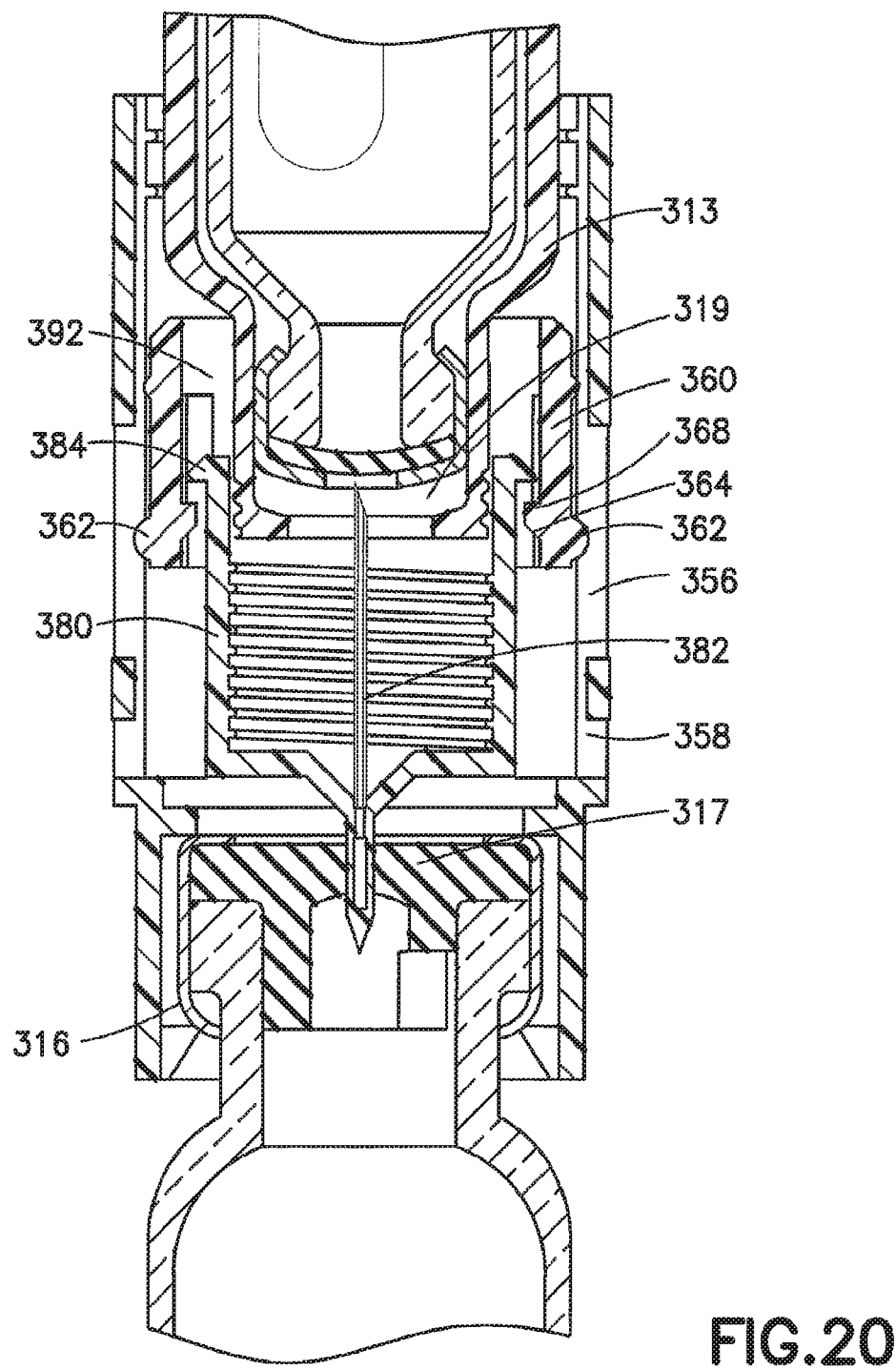
FIG. 20 is a partial cross-sectional front view of the transfer set of FIG. 17 in which the ring slide and cartridge have been advanced towards the vial in accordance with an embodiment of the present invention.
Figure 21:
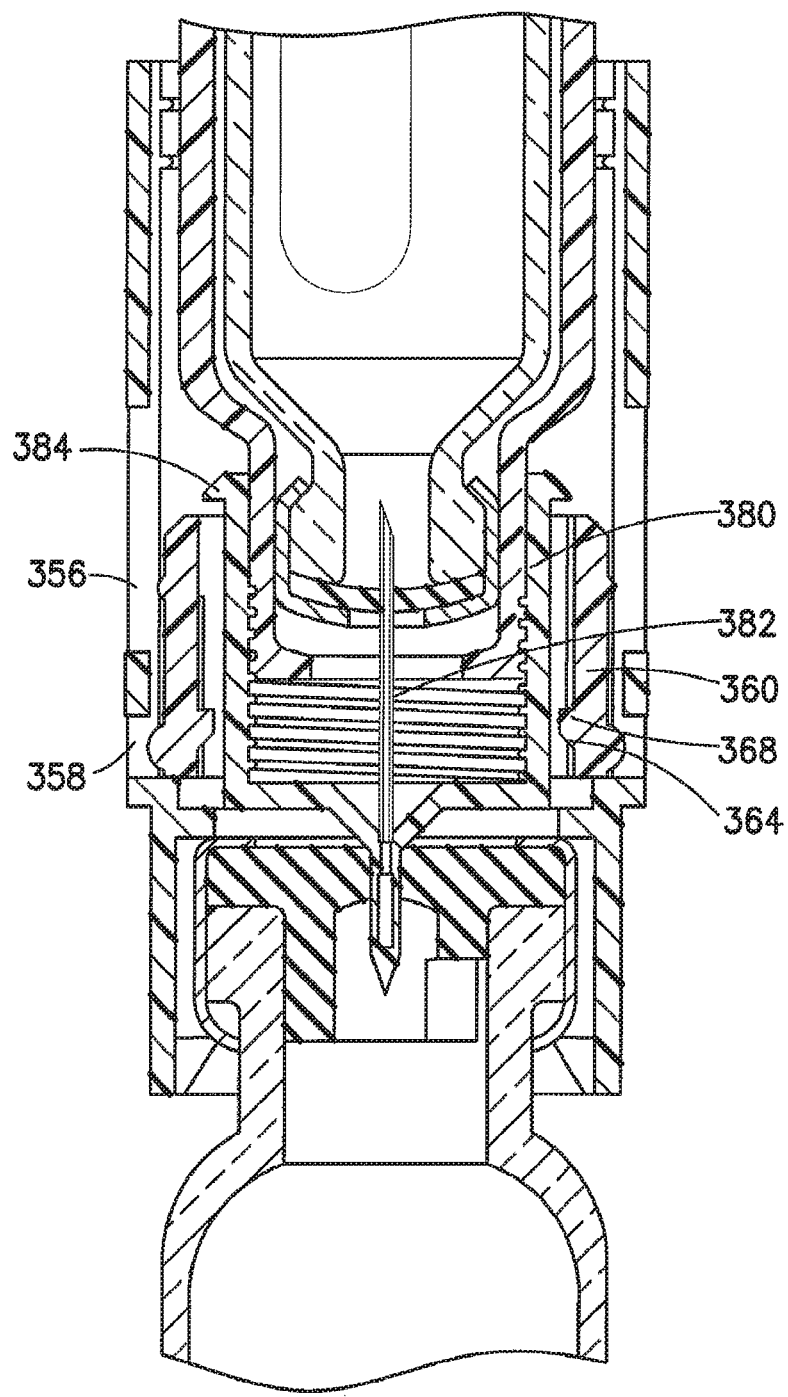
FIG. 21 is a partial cross-sectional front view of the transfer set of FIG. 17 in which the ring slide is locked in the final end of use position and in which the needle has pierced the septum of the cartridge and the vial in accordance with an embodiment of the present invention.
Figure 22:
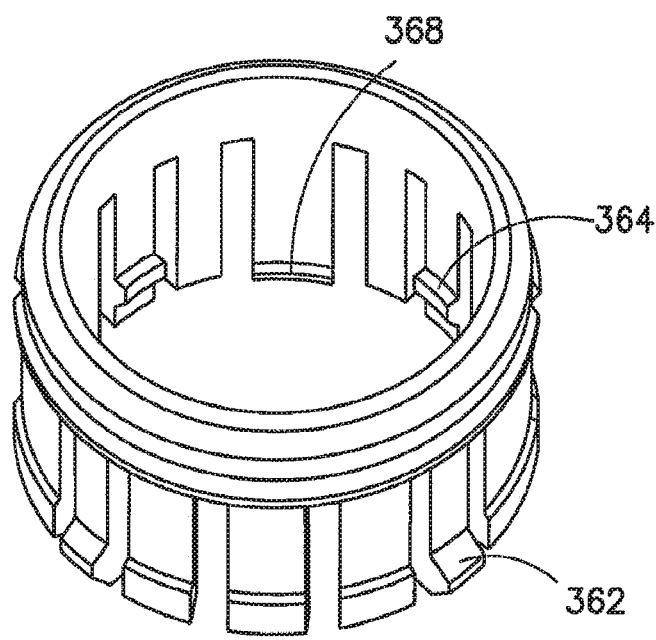
FIG. 22 is a perspective view of the ring slide of the adapter assembly of FIG. 18 in accordance with an embodiment of the present invention.
Figure 23:
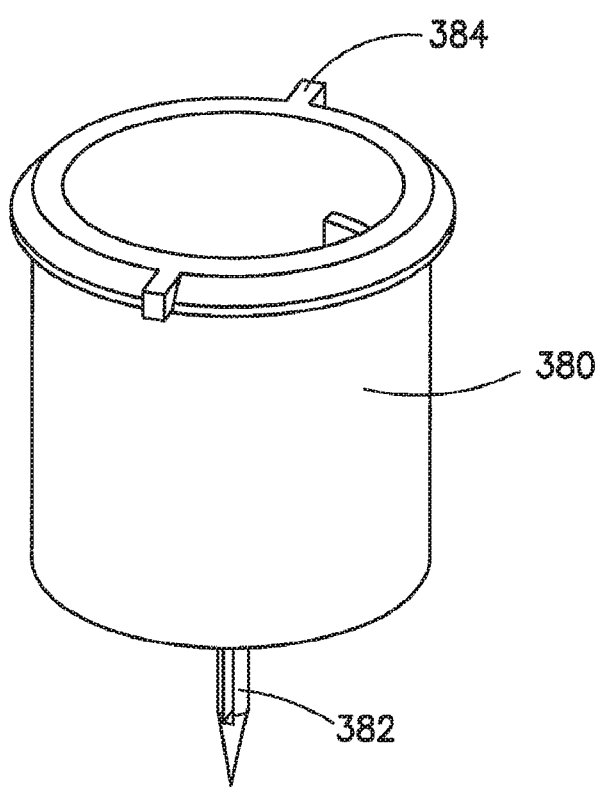
FIG. 23 is a perspective view of the needle holder of the adapter assembly of FIG. 18 in accordance with an embodiment of the present invention.

As the sliding ring 360 and float hub 380 are advanced through the adapter body 340, the push fingers 364 expand and open in the primary expansion window 356, thereby allowing the float hub 380 to slide into a cavity 392 formed by the ring slider 360, as shown in FIG. 20. In the final position, the push fingers 364 of the ring slider 360 expand to the secondary expansion window 358. The locking tabs 362 of the slider 360 engage with the secondary expansion window 358, thereby locking the ring slider 360 and float hub 380 in the final end of use position, as shown in FIG. 21. Once in this final locked position, the needle 382 cannot be exposed but remains in contact with the vial 316. Once the needle 382 is brought to the final (end of use) position, the user can inject the liquid component of the drug from the cartridge 318 into the vial 316 as described above. The user mixes the wet and dry components by shaking the assembly and then draws the mixed fluid back into the cartridge 318. The cartridge 318 and the cartridge holder assembly 312 may then be attached to a pen injector or other similar injection device.

What is claimed is:

1. An adapter assembly for establishing a bidirectional fluid connection between a cartridge and a vial comprising:
   a hollow housing having an open first end, an open second end adapted to engage the vial, and a wall extending therebetween; and
   a needle assembly comprising a needle holder, a needle connected to the needle holder comprising a first tip and a second tip, and a port configured to engage the cartridge, the needle assembly being disposed at least partially within the housing and being moveable through the housing from an initial position, in which the cartridge is engaged to the receiving port and the vial is engaged with the housing, to an end of use position, in which the first tip of the needle is engaged with the vial and the second tip of the needle is engaged with the cartridge, thereby establishing fluid communication between the cartridge and the vial,
   wherein the needle assembly is configured to engage a portion of the wall of the housing to maintain the needle assembly in the initial position, and wherein rotating the housing about the needle assembly disengages the needle assembly from the housing so that the needle assembly moves through the housing to the end of use position.

2. The adapter assembly of claim 1, wherein, in the initial position, the first tip of the needle and the second tip of the needle are isolated from both the cartridge and from the vial.

3. The adapter assembly of claim 1, wherein, in the end of use position, the first tip pierces a septum of the vial and the second tip pierces a septum of the cartridge.

4. The adapter assembly of claim 1, wherein the portion of the wall configured to engage the needle assembly comprises a rib protruding radially inwardly from the wall of the housing.

5. The adapter assembly of claim 4, wherein the needle holder comprises a notch, and wherein rotating the needle holder relative to the housing to align the rib and the notch disengages the needle assembly from the wall of the housing.

6. The adapter assembly of claim 1, wherein an interior surface of the wall of the housing comprises one or more longitudinal guide ribs engagable with one or more corresponding slots defined within the needle holder to support the needle holder as it moves within the housing.

7. The adapter assembly of claim 1, wherein during transition of the needle assembly from the initial position to the end of use position, the first tip engages the vial prior to the second tip engaging the cartridge.

8. The adapter assembly of claim 1, wherein the needle holder further comprises a tab configured to engage a portion of the wall of the housing to secure the needle assembly in the end of use position.

9. The adapter assembly of claim 8, wherein the portion of the wall of the housing which engages the tab comprises an opening in the wall of the housing, and wherein the tab is biased to extend into the opening to maintain the needle assembly in the end of use position.

10. The adapter assembly of claim 1, wherein the port comprises at least one screw channel adapted to receive a corresponding screw groove defined on a portion of the cartridge.

11. A transfer set for a cartridge and a vial, the transfer set comprising:
    a cartridge holder assembly configured to receive the cartridge; and
    an adapter assembly for establishing a fluid connection between the vial and the cartridge, the adapter assembly comprising:
      a hollow housing having an open first end, an open second end adapted to engage the vial, and a wall extending therebetween; and
      a needle assembly comprising a needle holder, a needle connected to the needle holder comprising a first tip and a second tip, and a port configured to engage the cartridge, the needle assembly being disposed at least partially within the housing and being moveable through the housing from an initial position, in which the cartridge is engaged to the port and the vial is engaged with the housing, to an end of use position, in which the first tip of the needle is engaged with the vial and the second tip of the needle is engaged with the cartridge, thereby establishing fluid communication between the cartridge and the vial,
    wherein the needle assembly is configured to engage a portion of the wall of the housing to maintain the needle assembly in the initial position, and wherein rotating the housing about the needle assembly disengages the needle assembly from the housing so that the needle assembly moves through the housing to the end of use position.

12. The transfer set of claim 11, wherein, in the initial position, the first tip of the needle and the second tip of the needle are isolated from both the cartridge and from the vial, and wherein, in the end of use position, the first tip pierces a septum of the vial and the second tip pierces a septum of the cartridge.

13. The transfer set of claim 11, wherein the portion of the wall configured to engage the needle assembly comprises a rib protruding radially inwardly from the wall of the housing.

14. The transfer set of claim 13, wherein the needle holder comprises a notch, and wherein rotating the needle holder relative to the housing to align the rib and the notch disengages the needle assembly from the wall of the housing.

15. The transfer set of claim 11, wherein an interior surface of the wall of the housing comprises one or more longitudinal guide ribs engagable with one or more corresponding slots defined within the needle holder to support the needle holder as it moves within the housing.

16. The transfer set of claim 11, wherein the needle holder further comprises a tab configured to engage a portion of the wall of the housing to secure the needle assembly in the end of use position.

17. The transfer set of claim 11, further comprising a plunger assembly comprising a stopper configured to be positioned in the cartridge and to move through the cartridge to expel fluid therefrom, a plunger extending from the stopper and through the cartridge holder assembly, and a thumb press at an end of the plunger for applying a distal force to the plunger.

18. The transfer set of claim 17, wherein the plunger further comprises a latch configured to engage the cartridge holder assembly to maintain the plunger in a compressed position.

19. The transfer set of claim 18, wherein the plunger further comprises a button for releasing the latch from the cartridge holder assembly so that the plunger can be retracted to draw fluid into the cartridge.

20. The transfer of claim 17, wherein the plunger further comprises a stop configured to engage the cartridge holder assembly to prevent the stopper from being removed from the cartridge.

* * * * *